United States Patent [19]
Baudy et al.

[11] Patent Number: 6,110,943
[45] Date of Patent: Aug. 29, 2000

[54] N-SUBSTITUTED (THIOPHEN-2-YL)-PIPERIDINES AND TETRAHYDROPYRIDINES AS SEROTONERGIC AGENTS

[75] Inventors: Reinhartd B. Baudy, Doylestown; Wayne E. Childers, Jr., Levittown, both of Pa.; Michael G. Kelly, Plainsboro, N.J.

[73] Assignee: American Home Products Corporation, Madison, N.J.

[21] Appl. No.: 09/286,753

[22] Filed: Apr. 6, 1999

[51] Int. Cl.[7] .................. A61K 31/445; C07D 409/04
[52] U.S. Cl. .................. 514/326; 514/336; 546/212; 546/280.4
[58] Field of Search ................ 546/212, 280.4; 514/326, 336

[56] References Cited

U.S. PATENT DOCUMENTS

| | | | |
|---|---|---|---|
| 3,518,274 | 6/1970 | Wallace | 546/234 |
| 5,525,600 | 6/1996 | Baudy | 514/212 |
| 5,789,422 | 8/1998 | Reichard et al. | 514/327 |

FOREIGN PATENT DOCUMENTS

99/45925  9/1999  WIPO.

*Primary Examiner*—Ceila Chang
*Attorney, Agent, or Firm*—Rebecca R. Barrett

[57] ABSTRACT

This invention provides compounds having the structure

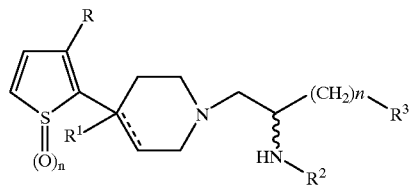

that are useful as antipsychotic, antidepressant and anxiolytic agents useful in the treatment and relief of the symptoms of these disease states.

13 Claims, No Drawings

N-SUBSTITUTED (THIOPHEN-2-YL)-PIPERIDINES AND TETRAHYDROPYRIDINES AS SEROTONERGIC AGENTS

BACKGROUND OF THE INVENTION

Compounds having selectivity for the 5-HT$_{1A}$ receptor are effective anxiolytic agents (buspirone, U.S. Pat. No. 3,717,634). The present invention provides novel compounds having 5-HT$_{1A}$ receptor selectivity.

DESCRIPTION OF THE INVENTION

In accordance with this invention, there is provided novel compounds having selectivity for the serotonergic 5HT1A receptor, useful in the treatment of central nervous system disorders. Compounds of the present invention have the structure:

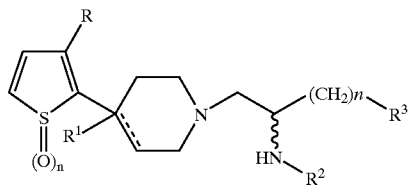

where:
- R is H, alkyl or 1–6 carbon atoms, alkenyl of 2–7 carbon atoms, alkynyl of 2–7 carbon atoms, CN, OR$^4$, COR$^4$, COOR$^4$, CONR$^4$R$^5$, perhaloalkyl of 1–6 carbon atoms, or halogen;
- the dotted line represents an optional double bond;
- R$^1$ H, OH or OR$^4$, or is absent if the optional double bond is present;
- R$^2$ is alkyl of 1–6 carbon atoms, alkenyl of 2–7 carbon atoms, alkynyl of 2–7 carbon atoms, phenyl, benzyl, COR$^4$ or COOR$^4$;
- R$^3$ is phenyl or heteroaryl;
- R$^4$ and R$^5$ are, independently, alkyl of 1–6 carbon atoms, alkenyl of 2–7 carbon atoms, alkynyl of 2–7 carbon atoms, phenyl, and benzyl; and n is 0, 1 or 2, or pharmaceutical salts thereof.

In some preferred embodiments of the present invention n is 1. It is preferred in other embodiments of the invention that R is OR$^4$. Preferably, R$^2$ is COR$^4$ or COOR$^4$. In still other preferred embodiments of the present invention R$^3$ is phenyl.

In still more preferred embodiments of the present invention n is 1, R is OR$^4$, R$^2$ is COR$^4$ or COOR$^4$ and R$^3$ is phenyl.

Suitable pharmaceutical salts of the present invention are those derived from such organic and inorganic acids as acetic, lactic, citric, tartaric, succinic, maleic, malonic, gluconic, hydrochloric, hydrobromic, phosphoric, nitric, sulfuric, methanesulfonic, and similarly known acceptable acids.

The term alkyl of 1–6 carbon atoms, alkenyl of 2–7 carbon atoms, and alkynyl of 2–7 carbon atoms include both straight chain as well as branched chain carbon chains. The term halogen refers to fluoro, chloro, bromo or iodo. The term perhaloalkyl refers to an alkyl group in which one or more hydrogen is replaced with halogen. An exemplary perhaloalkyl is trifluoromethyl. Heteroaryl, as used herein refers to 5 or 6 membered heterocyclic ring consisting of carbon atoms and from 1 to 3 heteroatoms selected from N, O and S. Exemplary heteroaryls include pyrazinyl, pyrrolyl, pyrazolyl, furanyl, thienyl, pyridyl, imidazolyl, pyrimidinyl, tetrahydropyrimidinyl, isoxazolyl, thiazolyl, and isothiazolyl.

In the generic structure provided above, when n is 0, the sulfur containing ring is a thiophene ring, when n is 1, the sulfur containing ring is a thiophene S-oxide and when n is 2 the sulfur containing ring is a thiophene S-dioxide.

The compounds of the present invention, by virtue of their configuration, exhibit stereoisomerism. Stereoisomeric centers can contain either R or S configuration or can be racemic with respect to such center or centers. Accordingly, compounds of the present invention include diastereomers, enantiomers, racemates and mixtures thereof.

The compounds of this invention are prepared by conventional methods. A 4-substituted piperidine is coupled in a Mitsunobu fashion (1) with a 2,3-substituted n-propane-1-ol to yield compounds of Formula 1.

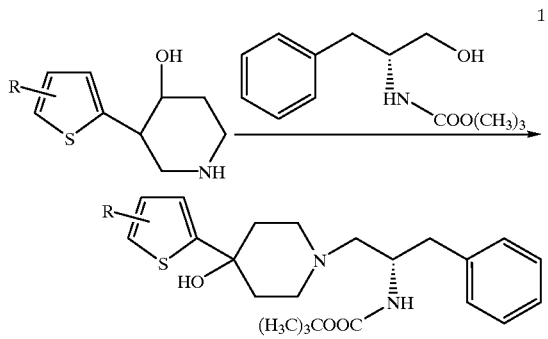

1

Treatment of compounds of Formula 1 with a dehydrating agent such as hydrochloric acid affords compounds of Formulas 2 and 3. Subsequent acylation of compounds of Formula 3 leads to compounds of Formula 4. Hydrogenation of compounds of Formula 4 affords compounds of Formula 5.

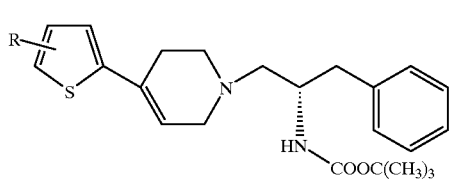

2

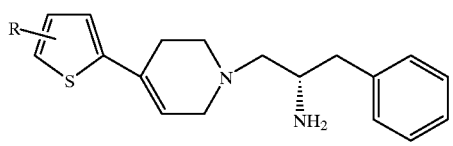

3

-continued

4

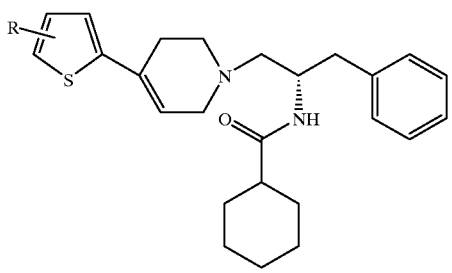

5

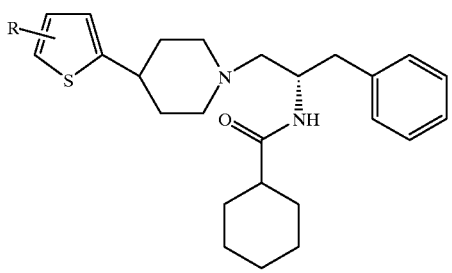

Representative compounds of the present invention were evaluated and determined to have high affinity for the serotonin 5-HT$_{1A}$ receptor by testing the compound's ability to displace [$^3$H] 8-OHDPAT (dipropylaminotetralin) from the 5-HT$_{1A}$ serotonin receptor following the procedure of Hall et al., *J. Neurochem.* 44, 1685 (1985). This standard pharmacological test procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., *Eur. J. Pharmacol.* 1986,129 (1–2)133–130).

The results of the standard experimental test procedure described in the preceding paragraph were as follows:

| Compound | 5-HT$_{1A}$ Binding (IC$_{50}$) |
|---|---|
| Example 1 | 80 nM |
| Example 2 | 1.6 nM |
| Example 3 | 0.78 nM |
| Example 4 | 1.1 nM |

Hence, the compounds of this invention demonstrated high affinity for the serotonin 5-HT$_{1A}$ receptor subtype, and are therefore useful in the treatment of multi-CNS disorders amenable to treatment with antipsychotic, antidepressant and anxiolytic agents. As such, compounds of the present invention may be administered to a mammal in need of antipsychotic, antidepressant or anxiolytic therapy in an amount sufficient to alleviate the symptoms of the disease state such as depression, paranoia, schizophrenia, anxiety, sleep disorders, panic, social phobias, obsessive compulsive disorders, sexual dysfunction, addiction, and related problems.

When administered for the treatment of the above disease states, the compounds of the invention may be administered to a mammal orally, parenterally, intranasally, intrabronchioally, transdermally, intravaginally, or rectally.

The compounds of the present invention can be formulated neat or with a pharmaceutical carrier to a mammal in need thereof. Carriers may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

(S)-{1-Benzyl-2-[4-hydroxy-4-(3-methoxy-thiophen-2-yl)-piperidin-1-yl]-ethyl}-carbamic acid tert-butyl ester 2.513 g (10 mmol) of (S)-(−)-2-(t-Butoxycarbonylamino)-3-phenyl-1-propanol was added at once to a magnetically stirred solution of 2.885 g (11 mmol)

triphenylphosphine in tetrahydrofuran (100 mL) at 0° C. Thereafter 1.9 mL (12 mmol) diethyl azodicarboxylate was added dropwise over 3 minutes while the temperature was maintained between 0 and 5° C. This was immediately followed by adding a solution of 2.14 g (10 mmol) of 4-hydroxy-4-(3-methoxy-thiophen-2-yl)-piperidine in 100 mL tetrahydrofuran. The reaction mixture was stirred at ambient temperature overnight, evaporated in vacuo to dryness and the residue flash chromatographed on 300 g silica gel using chloroform as eluant yielding 2.6 g of the title compound as a faintly yellow dense oil.

$^1$H NMR (DMSO-$d_6$, 400 Mhz) δ 1.3 (9H, s); 1.55 (2H, t) ; 2.2 (4H, q); 2.33 (2H, q); 2.58 (3H, m); 2.78 (1H, dd); 3.7 (3H, s); 3.78 (1H, m); 5.17 (1H, s); 6.58 (1H, d); 6.93 (1H, d); 7.17 (4H, t); 7.22 (2H, t).

EXAMPLE 2

(S)-{1-Benzyl-2-[4-(3-methoxy-thiophen-2-yl)-3,6-dihydro-2H-pyridin-1-yl]-ethyl}-carbamic acid tert-butyl ester A solution of 2.2 g (5 mmol) (S)-{1-benzyl-2-[4-hydroxy-4-(3-methoxy-thiophen-2-yl)-piperidin-1-yl]-ethyl}-carbamic acid tert-butyl ester in 20 mL tetrahydrofuran was treated at once with 20 mL 3M hydrochloric acid. The reaction mixture was stirred at ambient temperature overnight and then extracted with 50 mL diethyl ether. The remaining aqueous layer was basefied with sodium bicarbonate powder and extracted with chloroform (3×60 mL). The combined organic extract was dried over magnesium sulfate, filtered and evaporated to dryness in vacuo. The residue was flash chromatographed on 60 g silica gel. Elution with 2% methanol in chloroform yielded both, 100 mg of the title compound as a yellowish oil and 700 mg of (1S)-1-benzyl-2-[4-(3-methoxy-thiophen-2-yl)-3,6-dihydro-2H-pyridin-1-yl]-ethylamine as an amber oil.
Title compound:

$^1$H NMR (DMSO-$d_6$, 400 Mhz) δ 1.3 (9H, s); 2.3 (1H, dd); 2.39 (3H, m); 2.57 (3H, m); 2.81 (1H, dd); 3.05 (2H, bs); 3.78 (3H, s); 3.79 (1H, m); 6.17 (1H, bs); 6.62 (1H, d); 7.0 (1H, d); 7.18 (3H, m); 7.25 (3H, dd).

EXAMPLE 3

(S)-cyclohexanecarboxylic acid {1-benzyl-2-[4-(3-methoxy-thiophen-2-yl)-3,6-dihydro-2H-pyridin-1-yl]-ethyl}-amide A magnetically stirred solution of 0.5 g (1.52 mmol) of (1S)-1-Benzyl-2-[4-(3-methoxy-thiophen-2-yl)-3,6-dihydro-2H-pyridin-1-yl]-ethylamine and 0.42 ml (3.04 mmol) of triethylamine in 30 ml of dry dichloromethane was cooled in an ice bath under a dry nitrogen atmosphere. A solution of 0.25 g (1.67 mmol) of cyclohexane carbonyl chloride in 6 ml of dry dichloromethane was added dropwise over 10 minutes. The resulting solution was stirred at 4° C. for 1 hour and then the ice bath was removed and stirring was continued overnight (app. 18 hours), during which time the reaction came up to room temperature. TLC on silica gel (4% methanol/dichloromethane) revealed the absence of starting material and a new product (Rf=0.5). The reaction was concentrated on a rotary evaporator and partitioned between 75 ml of ethyl acetate and 50 ml of 1N aqueous sodium hydroxide. The organic layer was dried over anhydrous sodium sulfate and concentrated on a rotary evaporator. The resulting oil was purified by flash chromatography on silica gel (4% methanol/dichloromethane) to give 0.34 g of the desired (S)-cyclohexanecarboxylic acid {1-benzyl-2-[4-(3-methoxy-thiophen-2-yl)-3,6-dihydro-2H-pyridin-1-yl]-ethyl}-amide as oil which hardened upon exposure to vacuum. The compound was converted to its monofumerate·1.25 hydrate salt, yield=0.35 g (41%); mp=194–196° C.; $[α]^D_{25}$=+5.86 (EtOH, c=0.5).

Analysis for $C_{26}H_{34}N_2O_2S \cdot C_4H_4O_4 \cdot 1.25$ $H_2O$:

| | | | |
|---|---|---|---|
| Calculated: | C: 62.42; | H: 7.07; | N: 4.85 |
| Found: | C: 62.10; | H: 6.62; | N: 4.91 |

EXAMPLE 4

Cyclohexanecarboxylic acid {(1S)-1-benzyl-2-[4-(3-methoxy-thiophen-2-yl)-piperidin-1-yl]-ethyl}-amide A methanolic solution of the compound of example 3 (0.18 g in 10 ml) was hydrogenated at 50 psi over 10% Pd/C (20 mg) for 16 hours. The resulting mixture was purified by silica gel flash column chromatography (ethyl acetate) to afford the required product as a light yellow oil. The compound was converted to its fumarate salt which was obtained as a buff colored solid, mp 92–94° C.

Analysis for $C_{26}H_{36}N_2O_2S$ $3.0C_4H_4O_4$

| | | | |
|---|---|---|---|
| Calculated: | % C 57.86 | % H 6.13 | % N 3.55 |
| Found: | % C 57.34 | % H 6.1 | % N 3.66 |

What is claimed is:

1. A compound having the structure:

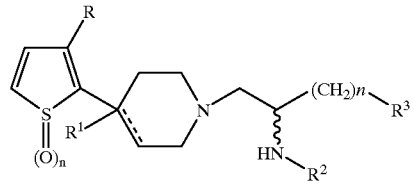

where:

R is H, alkyl or 1–6 carbon atoms, alkenyl of 2–7 carbon atoms, alkynyl of 2–7 carbon atoms, CN, $OR^4$, $COR^4$, $COOR^4$, $CONR^4R^5$, perhaloalkyl of 1–6 carbon atoms, or halogen;

the dotted line represents an optional double bond;

$R^1$ H, OH or $OR^4$, or is absent if the optional double bond is present;

$R^2$ is alkyl of 1–6 carbon atoms, alkenyl of 2–7 carbon atoms, alkynyl of 2–7 carbon atoms, phenyl, benzyl, $COR^4$ or $COOR^4$;

$R^3$ is phenyl or heteroaryl;

$R^4$ and $R^5$ are, independently, alkyl of 1–6 carbon atoms, alkenyl of 2–7 carbon atoms, alkynyl of 2–7 carbon atoms, phenyl, and benzyl; and n is 0, 1 or 2, or pharmaceutical salts thereof.

2. The compound of claim 1 wherein n is 1.
3. The compound of claim 1 wherein $R^3$ is phenyl.
4. The compound of claim 1 wherein R is $OR^4$.
5. The compound of claim 1 wherein $R^2$ is $COOR^4$.
6. The compound of claim 1 wherein $R^2$ is $COR^4$.
7. The compound of claim 1 which is the (S) stereoisomer.

8. The compound of claim 1 which is (S)-{1-Benzyl-2-[4-hydroxy-4-(3-methoxy-thiophen-2-yl)-piperidin-1-yl]-ethyl}-carbamic acid tert-butyl ester.

9. The compound of claim 1 which is (S)-{1-Benzyl-2-[4-(3-methoxy-thiophen-2-yl)-3,6-dihydro-2H-pyridin-1-yl]-ethyl}-carbamic acid tert-butyl ester.

10. The compound of claim 1 which is (S)-cyclohexanecarboxylic acid {1-benzyl-2-[4-(3-methoxy-thiophen-2-yl)-3,6-dihydro-2H-pyridin-1-yl]-ethyl}-amide.

11. The compound of claim 1 which is Cyclohexanecarboxylic acid {(1S)-1-benzyl-2-[4-(3-methoxy-thiophen-2-yl)piperidin-1-yl]ethyl]}amide.

12. A method of treating anxiety, psychosis, or depression in a mammal in need thereof which comprises administering to said mammal, an effective amount of a compound of the structure

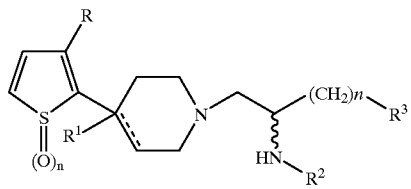

where:
R is H, alkyl or 1–6 carbon atoms, alkenyl of 2–7 carbon atoms, alkynyl of 2–7 carbon atoms, CN, $OR^4$, $COR^4$, $COOR^4$, $CONR^4R^5$, perhaloalkyl of 1–6 carbon atoms, or halogen;
the dotted line represents an optional double bond;
$R^1$ H, OH or $OR^4$, or is absent if the optional double bond is present;
$R^2$ is alkyl of 1–6 carbon atoms, alkenyl of 2–7 carbon atoms, alkynyl of 2–7 carbon atoms, phenyl, benzyl, $COR^4$, or $COOR^4$;
$R^3$ is phenyl or heteroaryl;
$R^4$ and $R^5$ are, independently, alkyl of 1–6 carbon atoms, alkenyl of 2–7 carbon atoms, alkynyl of 2–7 carbon atoms, phenyl, and benzyl; and n is 0, 1 or 2, or pharmaceutical salts thereof.

13. A pharmaceutical composition which comprises a therapeutically effective amount of a compound of the structure

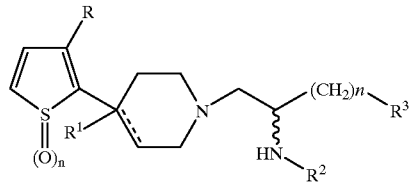

where:
R is H, alkyl or 1–6 carbon atoms, alkenyl of 2–7 carbon atoms, alkynyl of 2–7 carbon atoms, CN, $OR^4$, $COR^4$, $COOR^4$, $CONR^4R^5$, perhaloalkyl of 1–6 carbon atoms, or halogen;
the dotted line represents an optional double bond;
$R^1$ H, OH or $OR^4$, or is absent if the optional double bond is present;
$R^2$ is alkyl of 1–6 carbon atoms, alkenyl of 2–7 carbon atoms, alkynyl of 2–7 carbon atoms, phenyl, benzyl, $COR^4$ or $COOR^4$;
$R^3$ is phenyl or heteroaryl;
$R^4$ and $R^5$ are, independently, alkyl of 1–6 carbon atoms, alkenyl of 2–7 carbon atoms, alkynyl of 2–7 carbon atoms, phenyl, and benzyl; and n is 0, 1 or 2, or pharmaceutical salts thereof, and a pharmaceutical carrier.

* * * * *